United States Patent
Chaudhuri et al.

[11] Patent Number: 6,165,450
[45] Date of Patent: Dec. 26, 2000

[54] SPRAYABLE SUNSCREEN COMPOSITIONS

[75] Inventors: Ratan K. Chaudhuri, Lincoln Park, N.J.; George Majewski, Congers, N.Y.

[73] Assignee: EM Industries, Inc., Hawthorne, N.Y.

[21] Appl. No.: 09/303,625

[22] Filed: May 3, 1999

[51] Int. Cl.[7] .............................. A61K 7/42; A61K 7/44; A61K 7/00

[52] U.S. Cl. .............................. 424/59; 424/60; 424/400; 424/401

[58] Field of Search .............................. 424/59, 60, 400, 424/401

[56] References Cited

U.S. PATENT DOCUMENTS

| | | |
|---|---|---|
| 4,671,955 | 6/1987 | Palinczar . |
| 4,699,779 | 10/1987 | Palinczar . |
| 4,710,371 | 12/1987 | Palinczar . |
| 4,960,764 | 10/1990 | Figueroa, Jr. et al. . |
| 5,015,469 | 5/1991 | Yoneyama et al. . |
| 5,036,108 | 7/1991 | Asahi et al. . |
| 5,143,722 | 9/1992 | Hollenberg et al. . |
| 5,188,831 | 2/1993 | Nicoll et al. . |
| 5,196,187 | 3/1993 | Nicoll et al. . |
| 5,216,033 | 6/1993 | Pereira et al. . |
| 5,244,665 | 9/1993 | Natraj et al. . |
| 5,250,289 | 10/1993 | Boothroyd et al. . |
| 5,256,404 | 10/1993 | Martino et al. . |
| 5,292,503 | 3/1994 | Raleigh et al. . |
| 5,362,482 | 11/1994 | Yoneyama et al. . |
| 5,366,660 | 11/1994 | Tapley . |
| 5,399,342 | 3/1995 | Kryzsik . |
| 5,417,961 | 5/1995 | Nearn et al. . |
| 5,424,055 | 6/1995 | Hayashi et al. . |
| 5,427,771 | 6/1995 | Grollier et al. . |
| 5,476,643 | 12/1995 | Fogel . |
| 5,498,406 | 3/1996 | Nearn et al. . |
| 5,543,135 | 8/1996 | Dahms . |
| 5,543,136 | 8/1996 | Aldous . |
| 5,573,753 | 11/1996 | Tapley . |
| 5,579,524 | 11/1996 | Tanner et al. . |
| 5,599,529 | 2/1997 | Cowie . |
| 5,599,533 | 2/1997 | Stepniewski et al. . |
| 5,599,629 | 2/1997 | Gardner et al. . |
| 5,603,863 | 2/1997 | Dahms . |
| 5,603,940 | 2/1997 | Candau et al. . |
| 5,605,652 | 2/1997 | Tapley . |
| 5,605,678 | 2/1997 | Ascione et al. . |
| 5,607,664 | 3/1997 | Ascione et al. . |
| 5,609,854 | 3/1997 | Guerrero et al. . |
| 5,616,331 | 4/1997 | Allard et al. . |
| 5,635,163 | 6/1997 | Hansenne . |
| 5,645,842 | 7/1997 | Gruning et al. . |
| 5,650,146 | 7/1997 | Shaw . |
| 5,658,555 | 8/1997 | Ascione et al. . |
| 5,665,368 | 9/1997 | Lentini et al. . |
| 5,670,139 | 9/1997 | Allard et al. . |
| 5,688,831 | 11/1997 | El-Nokaly et al. . |
| 5,690,915 | 11/1997 | Eteve et al. . |
| 5,690,916 | 11/1997 | Kimura et al. . |
| 5,690,917 | 11/1997 | Eteve et al. . |
| 5,695,747 | 12/1997 | Forestier et al. . |
| 5,718,907 | 2/1998 | Labarre . |
| 5,730,993 | 3/1998 | Allard et al. . |
| 5,733,895 | 3/1998 | Forestier et al. . |
| 5,744,126 | 4/1998 | Horino et al. . |
| 5,756,110 | 5/1998 | Allard et al. . |
| 5,756,788 | 5/1998 | Mitchnick et al. . |
| 5,770,183 | 6/1998 | Linares . |
| 5,788,952 | 8/1998 | Gers-Barlag et al. . |
| 5,798,109 | 8/1998 | Yanagida et al. . |
| 5,804,167 | 9/1998 | Schonrock et al. . |
| 5,817,298 | 10/1998 | Galley et al. . |
| 5,827,508 | 10/1998 | Tanner et al. . |

OTHER PUBLICATIONS

Diffey, et al., A new substrate to measure sunscreen protection factors throughout the ultraviolet spectrum: J. Soc. Cosmet. Chem., 40, 127–133 (May/Jun. 1989), pp. 127–133.

*Primary Examiner*—Shelley A. Dodson
*Attorney, Agent, or Firm*—Millen, White, Zelano & Branigan, P.C.

[57] ABSTRACT

Stable, low viscosity, thixotropic, broad spectrum, sprayable sunscreen compositions suitable for topical application to human skin and hair are provided, along with a method for their preparation. The compositions comprise oil-in-water suspoemulsions containing dispersing agents to disperse inorganic sunscreen. The compositions are easy to apply to the skin and are practically non-whitening when applied on skin.

42 Claims, No Drawings

SPRAYABLE SUNSCREEN COMPOSITIONS

BACKGROUND OF THE INVENTION

The present invention relates to sprayable sunscreen compositions that are suitable for topical application to human skin and hair.

The damaging effects of sunlight on human skin have long been noted. In general terms, harmful ultra-violet (UV) rays, particularly those originating from sunlight, which penetrate the upper atmosphere and reach the earth's surface can be classified into two types: (i) high energy UV-B rays (290–320 nm wavelength) which are absorbed just above the dermis and are responsible for sunburn and tanning effects; and (ii) low energy UV-A rays (320–400 nm wavelength) which penetrate deeper into the skin (to the dermis and beyond), and which cause damaging effects that are more long term in nature, such as skin ageing.

Certain organic sunscreens composed of organic molecules that absorb the harmful ultra-violet rays have been proposed for use in mitigating the deleterious effects of ultra violet radiation. Organic sunscreen compounds which effectively absorb UV radiation in either the UV-A range or the UV-B range are known. However, a problem that exists with the organic sunscreens is that physiological damage to the body can occur following topical application of these sunscreens in quantities necessary to provide effective filtering of harmful ultra-violet radiation. As an alternative to organic sunscreens, certain inorganic substances such as titanium dioxide or zinc oxide which physically block exposure of the skin to ultra-violet rays have been employed.

A highly desirable method for delivering sunscreen compositions to the skin and hair is in the form of a finely dispersed spray. This form of product delivery offers improved product coverage on the skin or hair and allows easier application to difficult to reach areas. Such a spray is desirably delivered using a nonaerosol spray pump, which does not require the use of pressurized containers or special aerosolizing gases. The ability of such pump-driven delivery systems to deliver a product as a finely dispersed spray is critically dependent upon the viscosity of the composition at the exit port of the pump. As the viscosity of the composition decreases, the spray becomes more dispersed and yields a more desirable delivery. Conversely, as the viscosity increases, the spray becomes less dispersed and more stream-like, yielding a less desirable delivery.

It is well known in the art that stable oil-in-water emulsions are difficult to prepare at very low viscosities. Therefore, a need exists for stable oil-in-water compositions containing titanium oxide and/or zinc oxide, which have a high degree of stability and suspending power and yet are sufficiently thixotropic and low in viscosity that they can be effectively delivered to the skin or hair as fine spray using non-aerosol spray pumps.

SUMMARY OF THE INVENTION

Stable, low viscosity (1,000 to 10,000 Cps, Brookfield, @ 23° C.) broad-spectrum sunscreen formulations are difficult to prepare due to their inherent instability resulting in phase separation, agglomeration and sedimentation. An oil-in-water suspoemulsion system has now been developed that can be utilized to deliver inorganic sunscreens such as microfine titanium oxide and zinc oxide as part of a sprayable composition.

Sprayable sunscreen compositions, for topical application to human skin and hair, along with methods for their preparation, are provided. The compositions comprise oil-in-water suspoemulsions containing dispersing agents to disperse inorganic sunscreens. The compositions are useful for applying to human skin or hair for protection against ultraviolet radiation. Additionally, the inventive compositions are easy to apply and are practically non-whitening. The compositions of the invention are stable at high temperatures ( about 50° C.) and at low temperatures (about −10° C.).

The compositions of the invention are also advantageous in that they may comprise a hydrophobic or "oil" phase as low as 16% and remain stable. A minimal oil phase content is desirable for product cost-effectiveness and for allowing for a product with a non-greasy feel.

Also contemplated as part of the invention is a method of applying a sunscreen composition comprising spraying a composition of the invention onto the skin.

Compositions of the invention contain the following components (in % by weight):

(a) at least one dispersing agent of from about 0% to about 10%, preferably from about 0.4% to about 3%;

(b) at least one emulsifier of from about 2% to about 10%, preferably from about 3% to about 7%;

(c) at least one emollient or hydrophobic agent of from about 5% to about 30%, preferably from about 6% to about 20%, and more preferably from about 7% to about 18%;

(d) at least one inorganic sunscreen of from about 2% to about 15%, preferably from about 3% to about 10%, and more preferably from about 4% to about 8%;

(e) water of from about 55% to about 80%, preferably from about 60% to about 70%.

A water content of between about 55% to 80% is important for the following reasons. A water content of >80% may result in instability due to phase separation. A water content of <55% may result in instability due to phase separation and may result in an unsprayable formulation due to an increase in viscosity and a decrease in thixotropy.

The sunscreen compositions also optionally contain the following ingredients: thickening agents of from about 0.05% to about 1.0%, preferably about 0.1% to about 1.0%, and more preferably about 0.3% to about 0.5%; organic sunscreens of from about 0% to about 25%, preferably about 3% to about 15%; and other ingredients including preservatives, antioxidants, humectants, etc., generally in an amount of from about 0.1% to about 5%.

The compositions of the invention also optionally contain cosmetic adjuncts such as, for example, colorants, perfumes, and plant extracts such as Aloe vera, witch hazel, cucumber etc.

Sunscreen compositions which are waterproof are particularly desirable. Ingredients to enhance the water-proof nature of the composition may also be included such as, for example, compounds which form polymeric films such as dimethicone copolyol phosphate, diisostearoyl trimethylolpropane siloxysilicate, chitosan, dimethicone, polyethylene, PVP, and poly(vinylpyrrolidone/vinylacetate), PVP/Eicosene copolymer, Adipic acid/diethylene glycol/glycerin crosspolymer, etc..

Compositions of the invention have a viscosity range of from about 1,000 to about 10,000 Cps (Brookfield @ 23° C.), with a preferred range of from about 2,000 to 6,000 Cps (Brookfield @ 23° C.).

Compositions of the invention have a sun protection factor (SPF) range of from about 2 to about 60, with a preferred SPF range of from about 10 to about 45. The target SPF range can be achieved with a combination of both inorganic and organic sunscreen elements. SPF is determined, by techniques well known in the art, on human skin as described in the *Federal Register*, Aug. 25, 1978, Volume 43, Number 166, pages 38259–38269 ("Sunscreen Drug Products for Over-The-Counter Human Use", Food and Drug Administration). SPF values can also be approximated using in vitro models as described, for example, in *J. Soc. Cosmet. Chem.* 40:127–133 (May/June 1989).

Compositions of the invention offer protection from UV radiation with wavelengths of about 290 nm to 385 nm, and preferably from wavelengths in the range of from about 290 nm to about 370 nm.

Each of the components of the compositions of the invention is discussed in greater detail below.

(1) Dispersing Agents

Suitable dispersing agents include any compound useful for dispersing the inorganic sunscreen agent in either the water phase, the oil phase, or as part of the emulsion, including, for example, PPG-2 Ceteareth-9, polyquaternium 37, chitosan, steareth-10.

(2) Emulsifiers

Suitable emulsifiers include any agent useful for maintaining a stable emulsion, including, for example, PEG 100 stearate, glyceryl stearate, stearyl alcohol, cetyl alcohol, trideceth-6, PEG-75 stearate, ceteth-20, steareth-20, dimethicone copolyol phosphate, polysorbate 61, PPG-2, ceteareth-9, steareth-10, ceteth-2, hexadecyl D-glucoside, octadecyl D-glucoside, etc.

(3) Emollients or hydrophobic agents

Suitable emollients or hydrophobic agents include any agent useful for softening the skin or hair, including, for example, mineral oil, $C_{12-15}$ alkyl benzoate, diocyl adipate, octyl stearate, octyldodecanol, hexyl laurate, octyldodecyl neopentanoate, cyclomethicone, dicapryl ether, dimethicone, phenyltrimethicone, coco-caprylate.caprate, cetaryl isononanoate, isopropyl myristate, caprylic/capric triglycerides, propylene glycol dicaprylate/dicaprate, decyl oleate, etc.

(4) Inorganic Sunscreens

Inorganic sunscreens include, but are not limited to, microfine surface treated titanium dioxide and microfine untreated and surface treated zinc oxide. The titanium dioxide in the sunscreen compositions preferably has a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm. Examples of suitable hydrophobically modified titanium dioxide compositions include but are not limited to the following:

1. UV Titans® X161, M160, M262 (surface treated with stearic acid and alumina) (Kemira)
2. Eusolex® T-2000 (surface treated with alumina and simethicone) (Merck KGaA)
3. T-Cote® (surface treated with dimethicone) (SunSmart)
4. Mirasun® TiW60 (surface treated with silica and alumina) (Rhodia)
5. Tayaca MT100T (surface treated with aluminum stearate) (Tayaca)
6. Tayaca MT-100SA (surface treated with silica and alumina) (Tayaca)
7. Tayaca MT-500SA (surface treated with silica and alumina) (Tayaca)
8. Tioveil® EUT, FIN, FLO, FPT, GCM, GPT, IPM, MOTG, OP, TG, TGOP (surface treated with silica and alumina, 40% dispersion in a range of cosmetic vehicle) (ICI)
9. Eusolex® T-45D (surface treated with alumina and simethicone, 45% dispersion in isononoylnonaoate) (Merck KGaA)
10. Eusolex® T-Aqua (surface treated with aluminum hydroxide, 25% dispersion in water) (Merck KGaA)

Examples of suitable untreated and hydrophobically modified zinc oxide include but are not limited to the following:

1. Z-Cote® (uncoated microfine zinc oxide) (SunSmart)
2. Z-Cote® HP-1 (surface treated with dimethicone) (SunSmart)
3. Sachtotec® LA 10 (surface treated with lauric acid) (Sachtleben)
4. Sachtotec® (uncoated microfine zinc oxide) (Sachtleben)
5. Spectraveil® FIN, IPM, MOTG, OP, TG, TGOP (uncoated, 60% dispersion in a range of cosmetic vehicle) (ICI)
6. Z-sperse® TN (untreated, dispersion in C12–15 alkyl benzoate) (Collaborative)
7. Z-sperse® TN (untreated, dispersion in octydodecyl neopentanoate) (Collaborative)

(5) Thickening agents

Suitable thickening agents include any agent useful for increasing the emulsion viscosity. Such an increase in viscosity is important, for example, for aiding in the suspension of inorganic solids ($TiO_2$, ZnO) or for reducing oil droplet coalescence. Suitable thickening agents include, for example, polyquarternium 37, cetyl alcohol, polyquarternium 10, ammonium acrylate/acrylonitrile copolymers, and xanthan gum.

(6) Organic sunscreens

Suitable organic sunscreens include any organic agent capable of protecting the skin from UV radiation including, for example, octylmethoxycinnamate, octyl salicylate, homomenthyl salicylate, octocrylene, phenylbenzimidazole sulfonic acid, octyl dimethyl-para-amino benzoate, amylcinnamate, benzophenone-3, benzophenone-4, menthyl anthranilate etc.

(7) Preservatives

Suitable preservatives include any agent suitable for inhibiting the growth of biological organisms in the composition, including, for example, parahydroxy benzoate esters, DMDM hydantoin, phenoxyethanol, Kathone CG.

(8) Antioxidants

Suitable antioxidants include any agent suitable for retarding oxidation of the components of the composition. Suitable antioxidants include, for example, tocopherol, ascorbyl palmitate, citric acid, ascorbic acid, butylhydroxy toluene, butylhydroxyanisole and rosemary antioxidants, etc. For example a suitable commercial product for use as the antioxidant component is Oxynex® K (Rona/EM Industries), which contains tocopherol, ascorbyl palmitate, citric acid, ascorbic acid, and polyethylene glycol 400.

(9) Humectants

Suitable humectants include any hydrophilic agent with a stabilizing effect on the water content of the composition. Suitable humectants include, for example, glycerol, sorbitol, 2-pyrrolidone-5-carboxylate, butylene glycol, propylene glycol, ethoxydiglycol and polyethylene glycol such as PEG 200–600.

Sunscreens of the invention may be made by the following process. Other methods for making sunscreens of the invention are described in the Examples. A first phase comprising the hydrophobic ingredients including emollients, dispersing agents, emulsifiers, and, optionally, antioxidants, are combined by stirring and heating at temperature of from about 50° C. to about 80° C., preferably from about 55° C. to about 75° C., and most preferably from about 60° C. to 75° C., until all solids are dissolved. The inorganic sunscreen is then dispersed in the first phase with gentle stirring. A second phase comprising water, thickening agents, and other hydrophilic ingredients including, for example, humectants, emulsifiers, and preservatives are combined by stirring and heating at a temperature of from about 55° C. to about 80° C., preferably from about 60° C. to about 75° C., and most preferably at about 65° C. The second phase is then slowly added to the first phase while stirring at high speed. The mixture of the first and second phase is then gently homogenized until the temperature of the mixture is between about 35° C. to 40° C. to form an emulsion. Preservatives are added, and the emulsion is then stirred, preferably with an anchor mixer, and allowed to reach 25–30° C. before packaging.

If ethoxylated emulsifiers are being used and the preparation temperature exceeds 65° C., the emulsion may take a longer time to form as the result of phase separation due to oil coalescence during homogenization. If the preparation temperature is below 50° C., the resulting emulsion may form large droplets, which can affect the efficacy and stability of the sunscreen. If Emulgade PL 68/50 is being used, the oil and water phase temperatures are preferably between 70° C. and 80° C. for proper formation of the emulsion. Emulgade pellets dissolve at about 70° C. in the oil phase.

The compositions of the invention may be applied with any device having spraying means, including suitable aerosol or non-aerosol spray devices. Non-aerosol spray devices are preferred, and include for example, spray pumps such as the following: Eurogel Spray Pump (available from Seqquist Perfect, Cary Ill.), P1 spray pump (available from Precision, Ajax, Canada), and Calmar Spray Pumps, Calmar, Inc., City of Industry, Calif.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all parts and percentages are by weight unless otherwise indicated.

EXAMPLES

Example #1
(sunscreen agent: 8% Eusolex® T-2000 (amphiphilic microfine titanium dioxide))

| INCI Name | Trade Name | % w/w |
| --- | --- | --- |
| Phase A-1 | | |
| Isopropyl myristate | Emerest ® 2314 (Henkel) | 6.00 |
| Propylene glycol dicaprylate/dicaprate | Lexol PG-865 (Inolex) | 4.00 |
| Cocoglycerides | Myritol ® 331 (Henkel) | 5.00 |
| Dimethicone | Dow Corning 200 ®, 50 cst (Dow) | 2.00 |
| Diisostearoyl Trimethylolpropane Siloxy Silicate | SF 1318 (GE Silicones) | 2.00 |
| PPG-2 Ceteareth-9 | Eumulgin ® L (Henkel) | 0.50 |

| -continued | | |
| --- | --- | --- |
| INCI Name | Trade Name | % w/w |
| Hexadecyl D-glucoside, Octadecyl D-glucoside, cetyl/stearyl alcohol Phase A-2 | Emulgade ® PL68/50 (Henkel) | 3.30 |
| Titanium dioxide, Simethicone, Alumina Phase B-1 | Eusolex ® T-2000 (Rona) | 8.00 |
| Demineralized water | qs. | 63.65 |
| Glycerin USP | Emery 916 (Henkel) | 2.00 |
| Dimethicone copolyol phosphate Phase B-2 | Pecosil PS-100 (Phoenix Chemical) | 2.50 |
| Polyquaternium 37, Propylene glycol dicaprylate/dicaprate, PPG-1 trideceth-6 Phase C | Salcare SC 96 (Ciba) | 0.35 |
| Propylene glycol, DMDM | Paragon ™ II (McIntyre) | 0.70 |
| Hydantoin, Methylparaben, Propylparaben | | |
| Totals | | 100.00 |

The compositions of example 1 above, and examples 2–5 below are prepared as follows. A-1 ingredients are combined with stirring and heating to 70–75° C. until all solids are dissolved. The A-2 component is dispersed in the A-1 mixture with agitation. B-1 ingredients are combined with stirring and heating to 70–75° C. B-2 ingredients are then dispersed in B-1 with agitation. The A component is then added to the B component with vigorous mixing. The mixture of A and B is then gently homogenized while allowing the mixture to cool to 35–40° C. The C ingredients are then added to the A/B mixture with gentle homogenization until a uniform mixture is obtained. After homogenization, the mixture is stirred with an anchor mixture and allowed to reach 25° C. prior to packaging.

The composition of example 1 was determined to provide an SPF of 16 as determined by testing on five human subjects in accordance with the method described in the *Federal Register*, Aug. 25, 1978, Volume 43, Number 166, pages 38259–38269 ("Sunscreen Drug Products for Over-The-Counter Human Use", Food and Drug Administration).

Example #2
(sunscreen agent: 8% MT 500 SA (hydrophilic microfine titanium dioxide))

Example 2 is the same as Example 1 above with the following modification: Eusolex® T-2000 (amphiphilic microfine titanium dioxide) is replaced with 8% MT 500 SA (hydrophilic microfine titanium dioxide). The MT 500 SA is dispersed in the water phase during processing.

Example #3
(sunscreen agent: 8% MT 100 T (hydrophobic microfine titanium dioxide))

Example 3 is the same as Example 1 above with the following modification: Eusolex® T-2000 (amphiphilic microfine titanium dioxide) is replaced with 8% MT 100 T (hydrophobic microfine titanium dioxide).

Example #4
(sunscreen agent: 6% Eusolex ® T-2000 (amphiphilic microfine titanium dioxide) with 2% Z-cote® (microfine zinc oxide))

Example 4 is the same as Example 1 above with the following modification: Eusolex® T-2000 (amphiphilic microfine titanium dioxide) is reduced to 6% and 2% Z-cote® (microfine zinc oxide) is added.

Example #5
(sunscreen agent: 8% Eusolex® T-2000 (amphiphilic microfine titanium dioxide))

Example 5 is the same as Example 1 above with the following modifications: Emerest® 2314 is reduced to 4.0%; Myritol® 331 is replaced with 4.0% Lexol PG-865; SF 1318 is reduced to 1.5%; Emulgade® PL68/50 is replaced with Tegocare® 150; Salcare SC 96 is increased to 0.4%; water is increased to 68.1%; phases A and B are heated to 60–65° C.

Example #6
(5% Eusolex® T-2000 (amphiphilic microfine titanium dioxide) with organic UV filters)

| INCI Name | Trade Name | % w/w |
|---|---|---|
| Phase A-1 | | |
| Octyl methoxycinnamate | Eusolex ® 2292 (Rona) | 7.50 |
| Benzophenone-3 | Eusolex ® 4360 (Rona) | 2.50 |
| Dicapryl ether | Cetiol ® OE (Henkel) | 4.50 |
| Dimethicone | Dow corning 200 ®, 50 cst (Dow | 2.00 |
| Stearyl Alcohol | Crodacol S-70 (Croda) | 0.60 |
| PPG-2 Ceteareth-9 | Eumulgin ® L (Henkel) | 0.40 |
| Steareth-10 | Volpo 10 (Croda) | 0.50 |
| Glyceryl stearate, PEG-100 Stearate | Arlacel ® 165 (ICI) | 2.80 |
| Phase A-2 | | |
| Titanium Dioxide, Simethicone, Alumina | Eusolex ® T-2000 (Rona) | 5.00 |
| Phase B-1 | | |
| Demineralized water | qs. | 66.10 |
| Chitosan, water | Hydagen ® CMF (Henkel) | 2.00 |
| Glycerin USP | Emery 916 (Henkel) | 2.50 |
| Dimethicone copolyol phosphate | Pecosil PS-100 (Phoenix Chemical) | 2.50 |
| Phase B-2 | | |
| Polyquaternium 37, Mineral oil, PPG-1 trideceth-6 | Salcare SC 95 (Ciba) | 0.40 |
| Phase C | | |
| Propylene Glycol, DMDM Hydantoin, Methylparaben, propylparaben | Paragon ™ II (McIntyre) | 0.70 |
| Totals | | 100.00 |

The compositions of example 6 above and example 7 below are prepared as follows. A-1 ingredients are combined with stirring and heating to 60–65° C. until all solids are dissolved. A-2 components are dispersed in the A-1 mixture with agitation. B-1 ingredients are combined with stirring and heating to 60–65° C. B-2 ingredients are then dispersed in B-1 with agitation. The A component is then added to the B component with vigorous stirring. The mixture of A and B is then gently homogenized while allowing the mixture to cool to 35–40° C. The C ingredients are then added to the A/B mixture with gentle homogenization until a uniform mixture is obtained. After homogenization, the mixture is stirred with an anchor mixture and allowed to reach 25° C. prior to packaging.

The composition of example 6 was determined to provide an SPF of 31 as determined by testing on five human subjects in accordance with the method described in the Federal Register, Aug. 25, 1978, Volume 43, Number 166, pages 38259–38269 ("Sunscreen Drug Products for Over-The-Counter Human Use", Food and Drug Administration).

Example #7
(sunscreen agent: 5% Eusolex® T-2000 (amphiphilic microfine titanium dioxide) with organic UV filters)

Example 7 is the same as Example 6 above with the following modifications: Cetiol® OE is decreased to 4.0%. Emulgin®L is increased to 0.5%. Volpo 10 is eliminated. Arlacel® 165 is increased to 3.0%. Water is increased to 66.7%. Salcare® SC 95 is increased to 0.47%.

Example #8
(sunscreen agent: 4% Eusolex® T-2000 (amphiphilic microfine titanium dioxide) with organic UV filters)

| INCI Name | Trade Name | % w/w |
|---|---|---|
| Phase A-1 | | |
| Octyl methoxycinnamate | Eusolex ® 2292 (Rona) | 5.00 |
| Diocyl adipate | Dermol DOA (Alzo) | 4.00 |
| Dimethicone | Dow Corning 200 ®, 10 cst (Dow) | 2.00 |
| C12–15 Alkyl Benzoate | Finsolv TN (Finetex) | 3.00 |
| PPG-2 Ceteareth-9 | Eumulgin ® L (Henkel) | 0.50 |
| Diisostearoyl Trimethylolpropane Siloxy Silicate | SF 1318 (GE Silicones) | 1.50 |
| Glyceryl stearate, Cetyl alcohol, PEG-75 Stearate, Ceteth-20, Steareth-20 | Emulium delta (Gattefosse) | 3.30 |
| Phase A-2 | | |
| Titanium Dioxide, Simethicone, Alumina | Eusolex ® T-2000 (Rona) | 4.00 |
| Phase B-1 | | |
| Demineralized water | qs. | 70.50 |
| Butylene glycol | | 2.50 |
| Dimethicone copolyol phosphate | Pecosil PS-100 (Phoenix Chemical) | 2.50 |
| Phase B-2 | | |
| Polyquaternium 37, Propylene glycol dicaprylate/dicaprate, PPG-1 trideceth-6 | Salcare SC 96 (Ciba) | 0.47 |
| Phase C | | |
| Propylene glycol DMDM Hydantoin, Methylparaben, Propylparaben | Paragon ™ (McIntyre) | 0.73 |
| Totals | | 100.00 |

The compositions of example 8 above are prepared as follows. A-1 ingredients are combined with stirring and heating to 60–65° C. until all solids are dissolved. The A-2 components are dispersed in the A-1 mixture with agitation. B1 ingredients are combined with stirring and heating to 60–65° C. B-2 ingredients are dispersed in B-1 with agitation. The A component is then added to the B component with vigorous stirring. The mixture of A and B is then gently homogenized while allowing the mixture to cool to 40° C. The C ingredients are then added to the A/B mixture with gentle homogenization until a uniform mixture is obtained. After homogenization, the mixture is stirred with an anchor mixture and allowed to reach 25° C. prior to packaging.

The composition of example 1 was determined to provide an SPF of 18 as determined by testing on five human subjects in accordance with the method described in the Federal Register, Aug. 25, 1978, Volume 43, Number 166, pages 38259–38269 ("Sunscreen Drug Products for Over-The-Counter Human Use", Food and Drug Administration).

Example #9

(4% Eusolex® T-2000 (amphiphilic microfine titanium dioxide) with organic UV filters)

| INCI Name | Trade Name | % w/w |
|---|---|---|
| Phase A-1 | | |
| Octyl methoxycinnamate | Eusolex ® 2292 (Rona) | 5.00 |
| Cocoglycerides | Myritol ® 331 (Henkel) | 5.00 |
| Phenyl trimethicone | Dow Corning ® 556 (Dow) | 2.00 |
| Cetyl dimethicone | Abil Wax 9801 (Goldschmidt) | 3.00 |
| PPG-2 Ceteareth-9 | Eumulgin ® L (Henkel) | 1.00 |
| Octyldodecanol | Eutanol ® G (Henkel) | 4.00 |
| Steareth-10 | Volpo S-10 (Croda) | 0.90 |
| Steareth-2 | Volpo S-2 (Croda) | 0.80 |
| Hexadecyl D-glucoside, Octa decyl D-glycoside, cetyl/stearyl alcohol | Emulgade ® PL68/50 (Henkel) | 2.0 |
| Tocopherol, Ascorbyl palmitate, Citric acid, Ascorbic acid, Polyethylene glycol 400 | Oxynex ® K (Rona) | 0.10 |
| Phase A-2 | | |
| Titanium dioxide, Simethicone, Alumina | Eusolex ®T-2000 (Rona) | 4.00 |
| Phase B | | |
| Demineralized water | qs. | 69.00 |
| Butylene glycol | | 2.00 |
| Polyquaternium 37, propylene glycol dicaprylate/dicaprate, PPG-1 trideceth-6 | Salcare SC 96 (Ciba) | 0.20 |
| Phase C | | |
| Propylene Glycol, DMDM Hydantoin, Methylparaben, Propylparaben | Paragon ™ II (McIntyre) | 1.00 |
| Totals | | 100.00 |

The compositions of example 9 above are prepared as follows. A-1 ingredients are combined with stirring and heating to 75–80° C. until all solids are dissolved. The A-2 components are dispersed in the A-1 mixture with agitation. B ingredients are combined with stirring and heating to 70–75° C. The A component is then added to the B component with vigorous stirring. The mixture of A and B is then gently homogenized while allowing the mixture to cool to 40° C. The C ingredients are then added to the A/B mixture, followed by gentle homogenization until a uniform mixture is obtained. After homogenization, the mixture is stirred with an anchor mixture and allowed to reach 25° C. prior to packaging.

Example #10

(8.9% Eusolex® T-45-D (amphiphilic microfine titanium dioxide) with organic UV filters)

| INCI Name | Trade Name | % w/w |
|---|---|---|
| Phase A | | |
| Glyceryl Stearate (and) Steareth-25 (and) ceteth-20 (and) Stearyl | Tego Care 150 (Goldschmidt) | 4.00 |
| Isopropyl Myristate | Emerest ® 2314 (Henkel) | 5.00 |
| Octylmethoxycinnamate | Eusolex ® 2292 (Rona) | 6.00 |
| Dimethicone | Dow Corning 200 Fluid, 50 cst (Dow) | 2.00 |
| Isononyl Isononanoate, Polyglyceryl-6 Polyricinoleate, Titanium Dioxide, Simethicone, Alumina | Eusolex ® T45-D (Rona) | 8.90 |
| Adipic acid/diethylene glycol/glycerin crosspolymer | Lexorez ® 100 (Inolex) | 2.00 |
| Phase B-1 | | |
| Demineralized water | qs. | 65.80 |
| Glycerin | | 3.00 |
| Dimethicone copolyol phosphate | Pecosil PS-100 (Phoenix Chemical) | 2.00 |
| Phase B-2 | | |
| Polyquaternium 37, Propylene glycol dicaprylate/dicaprate, PPG-1 trideceth-6 | Salcare SC 96 (Ciba) | 0.50 |
| Phase C | | |
| Propylene glycol, DMDM Hydantoin, Methylparaben, Propylparaben | Paragon ™ II (McIntyre) | .80 |
| Totals | | 100.00 |

The compositions of example 10 above are prepared as follows. A ingredients are combined with stirring and heating to 55–60° C. until all solids are dissolved. B-1 ingredients are combined with stirring and heating to 55–60° C. B-2 ingredients are then dispersed in B-1 with agitation. The A component is then added to the B component with vigorous stirring. The mixture of A and B is then gently homogenized while allowing the mixture to cool to 40° C. The C ingredients are then added to the A/B mixture, followed by gentle homogenization until a uniform mixture is obtained. After homogenization, the mixture is stirred with an anchor mixture and allowed to reach 25° C. prior to packaging.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patent applications, patents, and publications cited herein are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A non-aerosol sprayable sunscreen composition comprising an oil-in-water emulsion which comprises:
   (a) at least one dispersing agent of from 0% to 10%;
   (b) at least one emulsifying agent of from 2% to 10%;
   (c) at least one emollient or hydrophobic agent of from 5% to 30%;
   (d) particles of at least one inorganic sunscreen of from 2% to 15%;
   (e) water of from 55% to 80%.

2. A non-aerosol sprayable sunscreen composition according to claim 1, further comprising at least one thickening agent of from 0.1% to 1.0%.

3. A non-aerosol sprayable sunscreen composition according to claim 1, wherein the particles of at least one inorganic sunscreen comprise titanium dioxide particles.

4. A non-aerosol sprayable sunscreen composition according to claim 3, wherein the particles of at least one inorganic sunscreen further comprise zinc oxide particles.

5. A non-aerosol sprayable sunscreen composition according to claim 1, wherein the particles of at least one inorganic sunscreen comprise zinc oxide particles.

6. A non-aerosol sprayable sunscreen composition according to claim 1, further comprising at least one organic sunscreen agent of from 0% to 25%.

7. A non-aerosol sprayable sunscreen composition according to claim 3, wherein the titanium dioxide particles are amphiphilic.

8. A non-aerosol sprayable sunscreen composition according to claim 3, wherein the titanium dioxide particles are hydrophobic.

9. A non-aerosol sprayable sunscreen composition according to claim 1, wherein the composition contains water in an amount of from 60% to 70% and particles of at least one inorganic sunscreen in an amount of from 3% to about 10%.

10. A non-aerosol sprayable sunscreen composition according to claim 9, further comprising at least one thickening agent of from 0.2% to 0.5%.

11. A non-aerosol sprayable sunscreen composition according to claim 9, wherein the particles of at least one inorganic sunscreen comprise titanium dioxide particles.

12. A non-aerosol sprayable sunscreen composition according to claim 11, wherein the particles of at least one inorganic sunscreen further comprise zinc oxide particles.

13. A non-aerosol sprayable sunscreen composition according to claim 9, wherein the particles of at least one inorganic sunscreen comprise zinc oxide particles.

14. A non-aerosol sprayable sunscreen composition according to claim 11, wherein the titanium dioxide particles are amphiphilic.

15. A non-aerosol sprayable sunscreen composition according to claim 11, wherein the titanium dioxide particles are hydrophobic.

16. A non-aerosol sprayable sunscreen composition according to claim 1, wherein the sunscreen composition has an in vivo sun protection factor (SPF) of from 2 to 60.

17. A method of making a non-aerosol sprayable sunscreen composition of claim 1 comprising the steps of:
(a) mixing a first phase comprising the emollient and the emulsifying agent;
(b) dispersing the particles of at least one inorganic sunscreen in the first phase;
(c) mixing a second phase comprising water and other water soluble ingredients;
(d) adding the first phase to the second phase under conditions sufficient to form a mixture of the first phase and the second phase;
(e) homogenizing the mixture of the first phase and the second phase to form an emulsion.

18. A method of making a non-aerosol sprayable sunscreen composition of claim 2 comprising the steps of:
(a) mixing a first phase comprising the emollient and the emulsifying agent;
(b) dispersing the particles of at least one inorganic sunscreen in the first phase;
(c) mixing a second phase comprising water, the thickening agent, and other water soluble ingredients;
(d) adding the first phase to the second phase under conditions sufficient to form a mixture of the first phase and the second phase;
(e) homogenizing the mixture of the first phase and the second phase to form an emulsion.

19. A method of making a non-aerosol sprayable sunscreen composition of claim 3 comprising the steps of:
(a) mixing a first phase comprising the emollient and the emulsifying agent;
(b) dispersing the particles of titanium dioxide in the first phase;
(c) mixing a second phase comprising water and other water soluble ingredients;
(d) adding the first phase to the second phase under conditions sufficient to form a mixture of the first phase and the second phase;
(e) homogenizing the mixture of the first phase and the second phase to form an emulsion.

20. A method of making a non-aerosol sprayable sunscreen composition of claim 6 comprising the steps of:
(a) mixing a first phase comprising the emollient, the emulsifying agent, and the organic sunscreen agent;
(b) dispersing the particles of at least one inorganic sunscreen in the first phase;
(c) mixing a second phase comprising water and other water soluble ingredients;
(d) adding the first phase to the second phase under conditions sufficient to form a mixture of the first phase and the second phase;
(e) homogenizing the mixture of the first phase and the second phase to form an emulsion.

21. A method of making a non-aerosol sprayable sunscreen composition of claim 9, comprising the steps of:
(a) mixing a first phase comprising the emollient and the emulsifying agent;
(b) dispersing the particles of at least one inorganic sunscreen in the first phase;
(c) mixing a second phase comprising water and other water soluble ingredients;
(d) adding the first phase to the second phase under conditions sufficient to form a mixture of the first phase and the second phase;
(e) homogenizing the mixture of the first phase and the second phase to form an emulsion.

22. A method of making a non-aerosol sprayable sunscreen composition of claim 10, comprising the steps of:
(a) mixing a first phase comprising the emollient and the emulsifying agent;
(b) dispersing the particles of at least one inorganic sunscreen in the first phase;
(c) mixing a second phase comprising water, the thickening agent, and other water soluble ingredients;
(d) adding the first phase to the second phase under conditions sufficient to form a mixture of the first phase and the second phase;
(e) homogenizing the mixture of the first phase and the second phase to form an emulsion.

23. A method of making a non-aerosol sprayable sunscreen composition of claim 11, comprising the steps of:
(a) mixing a first phase comprising the emollient and the emulsifying agent;
(b) dispersing the titanium dioxide particles in the first phase;
(c) mixing a second phase comprising water and other water soluble ingredients;
(d) adding the first phase to the second phase under conditions sufficient to form a mixture of the first phase and the second phase;

(e) homogenizing the mixture of the first phase and the second phase to form an emulsion.

24. A method of applying a non-aerosol sprayable sunscreen composition comprising spraying onto skin a composition according to claim 2.

25. A method of applying a non-aerosol sprayable sunscreen composition comprising spraying onto skin a composition according to claim 3.

26. A non-aerosol sprayable sunscreen composition comprising an oil-in-water emulsion which comprises:

(a) at least one dispersing agent of from 0% to 10%;

(b) at least one emulsifying agent of from 2% to 10%;

(c) at least one emollient or hydrophobic agent of from 5% to 30%;

(d) particles of at least one inorganic sunscreen of from 2% to 15%;

(e) water of from 55% to 80%;

wherein the composition is prepared by a process comprising the steps of:

(a) mixing a first phase comprising the emollient and the emulsifying agent;

(b) dispersing the particles of at least one inorganic sunscreen in the first phase;

(c) mixing a second phase comprising water and other water soluble ingredients;

(d) adding the first phase to the second phase under conditions sufficient to form a mixture of the first phase and the second phase;

(e) homogenizing the mixture of the first phase and the second phase to form an emulsion.

27. A non-aerosol sprayable sunscreen composition according to claim 26, wherein of from 0.1% to 1.0% of at least one thickening agent is mixed with the second phase.

28. A non-aerosol sprayable sunscreen composition according to claim 26, wherein the particles of at least one inorganic sunscreen comprise titanium dioxide particles.

29. A non-aerosol sprayable sunscreen composition according to claim 28, wherein the particles of at least one inorganic sunscreen further comprise zinc oxide particles.

30. A non-aerosol sprayable sunscreen composition according to claim 26, wherein the particles of at least one inorganic sunscreen comprise zinc oxide particles.

31. A non-aerosol sprayable sunscreen composition according to claim 26, wherein of from 0% to 25 % of at least one organic sunscreen is mixed with the first phase.

32. A non-aerosol sprayable sunscreen composition according to claim 28, wherein the titanium dioxide particles are amphiphilic.

33. A non-aerosol sprayable sunscreen composition according to claim 28, wherein the titanium dioxide particles are hydrophobic.

34. A non-aerosol sprayable sunscreen composition according to claim 28, wherein the composition contains water in an amount of from 60% to 70% and particles of at least one inorganic sunscreen in an amount of from 3% to about 10%.

35. A container containing a non-aerosol sprayable sunscreen composition, wherein said container comprises non-aerosol spraying means and wherein said non-aerosol sprayable sunscreen composition comprises (a) at least one dispersing agent of from 0% to 10%;

(b) at least one emulsifying agent of from 2% to 10%;

(c) at least one emollient or hydrophobic agent of from 5% to 30%;

(d) particles of at least one inorganic sunscreen of from 2% to 15%;

(e) water of from 55% to 80%.

36. A container according to claim 35, wherein the non-aerosol sprayable sunscreen composition further comprises of from 0.2% to 0.5% of at least one thickening agent.

37. A container according to claim 35, wherein the particles of at least one inorganic sunscreen comprise titanium dioxide particles.

38. A container according to claim 37, wherein the particles of at least one inorganic sunscreen further comprise zinc oxide particles.

39. A container according to claim 35, wherein the particles of at least one inorganic sunscreen comprise zinc oxide particles.

40. A container according to claim 37, wherein the titanium dioxide particles are amphiphilic.

41. A container according to claim 37, wherein the titanium dioxide particles are hydrophobic.

42. A container according to claim 35, wherein the non-aerosol sprayable sunscreen composition has an in vivo sun protection factor (SPF) of from 2 to 60.

* * * * *